United States Patent
Beight et al.

(10) Patent No.: US 6,924,296 B2
(45) Date of Patent: Aug. 2, 2005

(54) ANTITHROMBOTIC AGENTS

(75) Inventors: Douglas Wade Beight, Frankfort, IN (US); John Joseph Masters, Fishers, IN (US); Jason Scott Sawyer, Indianapolis, IN (US); Robert Theodore Shuman, Sedona, AZ (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 30 days.

(21) Appl. No.: 10/333,624

(22) PCT Filed: Aug. 6, 2001

(86) PCT No.: PCT/US01/21130

§ 371 (c)(1),
(2), (4) Date: Jan. 17, 2003

(87) PCT Pub. No.: WO02/14308

PCT Pub. Date: Feb. 21, 2002

(65) Prior Publication Data

US 2004/0010017 A1 Jan. 15, 2004

Related U.S. Application Data

(60) Provisional application No. 60/225,926, filed on Aug. 17, 2000.

(51) Int. Cl.[7] ..................... A61K 31/445; C07D 401/14
(52) U.S. Cl. ...................................... 514/318; 546/193
(58) Field of Search ........................... 514/318; 546/193

(56) References Cited

FOREIGN PATENT DOCUMENTS

| WO | WO 99/00121 | 1/1999 |
|----|-------------|--------|
| WO | WO 99/00126 | 1/1999 |
| WO | WO 99/00127 | 1/1999 |
| WO | WO 99/00128 | 1/1999 |
| WO | WO 00/39092 | 7/2000 |
| WO | WO 00/39111 | 7/2000 |
| WO | WO 00/39117 | 7/2000 |
| WO | WO 00/39118 | 7/2000 |
| WO | WO 02/10154 | 2/2002 |

OTHER PUBLICATIONS

Wyngaarden et al. "Cecil Textbook of medicine" Saunders, p. 247–248, 1005–1006 (1983).*
McCarthy et al. preparation of substituted diamine . . . CA 131:310284 (1999).*
Vacca, Joseph P. (Annette M. Doherty Section Editor), Annual Reports in Medicinal Chemistry, (1998), 33, 81–90.

* cited by examiner

Primary Examiner—Celia Chang
(74) Attorney, Agent, or Firm—Thomas E. Jackson; Arvie J. Anderson

(57) ABSTRACT

This application relates to a compound of formula I (or a prodrug thereof or a pharmaceutically acceptable salt of the compound or prodrug thereof) as defined herein, pharmaceutical compositions thereof, and its use as an inhibitor of factor Xa, as well as a process for its preparation and intermediates therefor.

8 Claims, No Drawings

ANTITHROMBOTIC AGENTS

This application claims the benefit of U.S. Provisional Application No. 60/225,926, filed Aug. 17, 2000, which is incorporated by reference herein in its entirety.

This invention relates to antithrombotic aromatic compounds which demonstrate activity as inhibitors of factor Xa and, accordingly, which are useful anticoagulants in mammals. In particular it relates to aromatic compounds having high anticoagulant activity, and antithrombotic activity. Thus, this invention relates to new inhibitors of factor Xa, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Joseph P. Vacca (Annette M. Doherty Section Editor), *Annual Reports in Medicinal Chemistry*, (1998), 33, 81–90.

Although the heparins and coumarins are effective anticoagulants, no commercial drug has yet emerged from the small synthetic molecules; and despite the continuing promise for this class of compounds, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent inhibitors of factor Xa which may have high bioavailability following oral administration.

According to the invention there is provided a compound of formula I (or a pharmaceutically acceptable salt thereof)

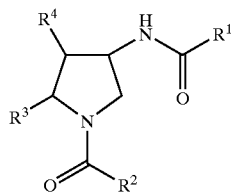

wherein one of $R^1$ and $R^2$ is $Q^1$; the other of $R^1$ and $R^2$ is $Q^2$;

wherein $Q^1$ is 2-pyridinyl (which may bear a methyl, methoxy, methylthio, fluoro or chloro substituent at the 5-position) or 3-pyridinyl (which may bear a methyl, fluoro or chloro substituent at the 6-position); or $Q^1$ is phenyl which may bear one, two or three substituents at the 3-, 4- or 5-position(s) independently selected from halo, cyano, carbamoyl, aminomethyl, methyl, methoxy, difluoromethoxy, hydroxymethyl, formyl, vinyl, dimethylamino, amino, hydroxy and 3,4-methylenedioxy, and in addition, the phenyl may bear a 2-chloro or 2-fluoro substituent; or $Q^1$ is

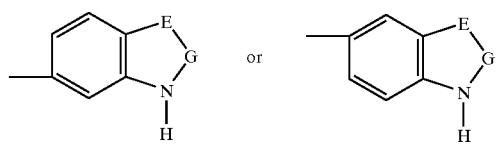

wherein

—E—G—NH— is —$CH_2$—$CH_2$—NH—, —$C(R^a)$=CH—NH—, —$C(R^a)$=N—NH—, —N=CH—NH— or —N=N—NH— in which $R^a$ is hydrogen, fluoro, chloro, bromo or methyl;

$Q^2$ is

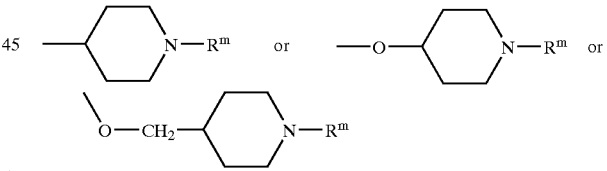

in which $R^m$ is (1–4C)alkyl, cyclohexyl, 4-tetrahydropyranyl, phenyl, 4-pyridyl or 2-pyrimidinyl;

when $R^2$ is $Q^1$, then $R^3$ is H, COOH, N-(methyl)benzenesulfonylamino or phenyl (which may be substituted at the 3- or 4-position with methyl, chloro or fluoro) and $R^4$ is H; and when $R^2$ is $Q^2$, then $R^3$ is H and $R^4$ is H, COOH, methyl, N-(methyl)benzenesulfonylamino, unsubstituted phenyl or phenyl (which may be substituted at the 3- or 4-position with methyl, chloro or fluoro;

or a prodrug of the compound of formula I;

or a pharmaceutically acceptable salt of the compound of formula I or prodrug thereof.

A particular compound of formula I is a compound of formula I (or a pharmaceutically acceptable salt thereof)

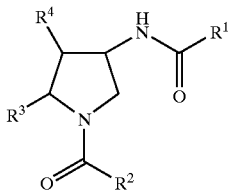

wherein
one of $R^1$ and $R^2$ is $Q^1$; the other of $R^1$ and $R^2$ is $Q^2$;
wherein
$Q^1$ is 2-pyridinyl (which may bear a methyl, methoxy, methylthio, fluoro or chloro substituent at the 5-position) or 3-pyridinyl (which may bear a methyl, fluoro or chloro substituent at the 6-position); or
$Q^1$ is phenyl which may bear one, two or three substituents at the 3-, 4- or 5-position(s) independently selected from halo, cyano, carbamoyl, aminomethyl, methyl, methoxy, difluoromethoxy, hydroxymethyl, formyl, vinyl, amino, hydroxy and 3,4-methylenedioxy, and in addition, the phenyl may bear a 2-chloro or 2-fluoro substituent; or
$Q^1$ is

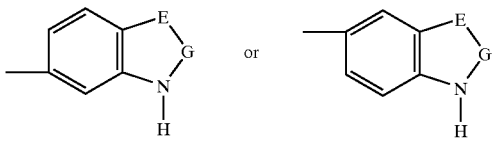

wherein
—E—G—NH— is —$CH_2$—$CH_2$—NH—, —C($R^a$)=CH—NH—, —C($R^a$)=N—NH—, —N=CH—NH— or —N=N—NH— in which $R^a$ is hydrogen, fluoro, chloro, bromo or methyl;
$Q^2$ is

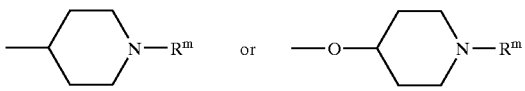

in which $R^m$ is (1–4C)alkyl, cyclohexyl, 4-tetrahydropyranyl, phenyl, 4-pyridyl or 2-pyrimidinyl;
when $R^2$ is $Q^1$, then $R^3$ is H, COOH, N-(methyl)benzenesulfonylamino or phenyl (which may be substituted at the 3- or 4-position with methyl, chloro or fluoro) and $R^4$ is H; and
when $R^2$ is $Q^2$, then $R^3$ is H and $R^4$ is H, COOH, methyl, N-(methyl)benzenesulfonylamino, unsubstituted phenyl or phenyl which may be substituted at the 3- or 4-position with methyl, chloro or fluoro;
or a prodrug of the compound of formula I;
or a pharmaceutically acceptable salt of the compound of formula I or prodrug thereof.

As used herein, the expression a compound of formula I or the expression a compound of the invention includes the compound and any conventional prodrug thereof, as well as a pharmaceutically acceptable salt of said compound or prodrug.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In this specification, the following definitions are used, unless otherwise described: Halo is bromo, chloro or fluoro. Alkyl, alkoxy, etc. denote both straight and branched groups; but reference to an individual radical such as "propyl" embraces only the straight chain ("normal") radical, a branched chain isomer such as "isopropyl" being specifically denoted.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–4C)alkyl is methyl, ethyl, isopropyl, or 2-butyl; and more particularly is ethyl, isopropyl, or 2-butyl. A particular value for halo is fluoro or chloro, and more particularly is fluoro.

A particular value for $Q^1$ is 5- or 6-indolyl. A more particular value for $Q^1$ is 6-indolyl. A particular value for $Q^2$ is 1-(4-pyridinyl)piperin-4-yl. When $R^2$ is $Q^1$, particular values for $R^3$ are H or COOH, and more particularly H, and for $R^4$ is H. When $R^2$ is $Q^2$, a particular value for $R^4$ is H and for $R^3$ is H.

A more particular compound of formula I is one wherein one of $R^1$ and $R^2$ is $Q^1$ and the other of $R^1$ and $R^2$ is $Q^2$;

$Q^1$ is

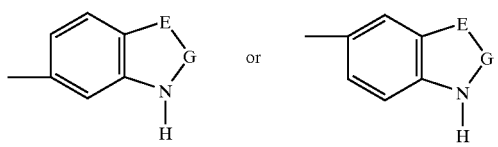

wherein
—E—G—NH— is —CH$_2$=CH$_2$—NH—;
$Q^2$ is

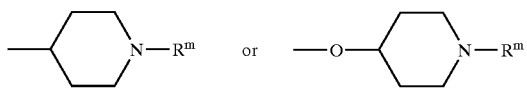

in which $R^m$ is 4-pyridyl;
when $R^2$ is $Q^1$, then $R^3$ is H or COOH and $R^4$ is H; and
when $R^2$ is $Q^2$, then $R^3$ is H and $R^4$ is H.

Another more particular compound of formula I is one wherein
$R^1$ is $Q^2$;
$R^2$ is $Q^1$;
$Q^1$ is 6-indolyl;
$Q^2$ is 1-(4-pyridinyl)piperin-4-yl;
$R^3$ is H; and
$R^4$ is H.

A further more particular compound of formula I is one wherein
$R^1$ is $Q^1$;
$R^2$ is $Q^2$;
$Q^1$ is 6-indolyl;
$Q^2$ is 1-(4-pyridinyl)piperin-4-yl;
$R^3$ is H; and
$R^4$ is H.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms since there may be more than one asymmetric center. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

A compound of formula I may be prepared by processes which include processes known in the chemical art for the production of any known compounds of formula I or of structurally analogous compounds or by a novel process described herein. A process for the preparation of a novel compound of formula I (or a pharmaceutically acceptable salt thereof), novel processes for the preparation of a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a novel compound of formula I (or a pharmaceutically acceptable salt thereof) as provided in any of the above descriptions which is selected from any of those described in the examples, including the following:

(A) For a compound of formula I in which $R^1$ is $Q^1$, acylating the amino group of a corresponding compound of formula II

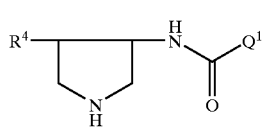

using a corresponding acid of formula $Q^2$-COOH (III) or an activated derivative thereof.

For a carboxylic acid, a typical activated derivative includes an ester (particularly a lower alkyl ester such as the methyl or ethyl ester), an acid halide (particularly the acid chloride), and an activated ester or anhydride (including the 4-nitrophenyl ester and an activated ester or anhydride derived from a coupling reagent).

The acylation may be completed, for example, using a similar procedure to that described in Example 1, Part D.

(B) For a compound of formula I in which $R^2$ is $Q^1$, acylating the amino group of a corresponding compound of formula IV

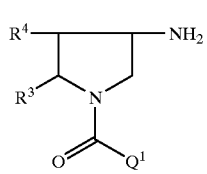

using a corresponding acid of formula $Q^2$-COOH (III) or an activated derivative thereof, for example, using a similar procedure to that described in Example 1, Part D.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials.

Novel intermediate or starting material compounds provide further aspects of the invention.

An example is a compound of formula II

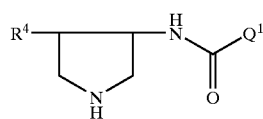

wherein $Q^1$ and $R^4$ have values as previously defined above.

Another example is a compound of formula IV

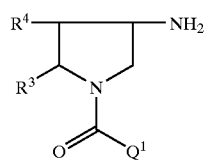

wherein $Q^1$, $R^3$ and $R^4$ have values as previously defined above.

Selective methods of substitution, protection and deprotection are well known in the art for preparation of a compound such as one of formula II and formula IV discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

Also, there is provided a compound of formula I (or prodrug or salt) having any of the definitions herein for use as an antithrombotic agent.

In addition, there is provided the use of a compound of formula I having any of the definitions herein for the manufacture of a medicament for treatment of a thromboembolic disorder.

In a further embodiment the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mf/tablet) |
| --- | --- |
| Active ingredient | 250 |
| Cellulose, microcrystalline | 400 |

-continued

|  | Quantity (mf/tablet) |
|---|---|
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
|---|---|
| Active ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

Enzyme+I⇌Enzyme–I

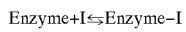

$$Kass = \frac{[Enzyme-I]}{[(Enzyme) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 μL buffer (0.03 M Tris, 0.15 M NaCl pH 7) in each well, followed by 25 μL of inhibitor solution (in 100% methanol, or in 50% v:v aqueous methanol) and 25 μL enzyme solution; within two minutes, 150 μL aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyroglutamyl-Gly-Arg-pNA.

Kass is calculated for a range of concentrations of test compounds and the mean value reported in units of liter per mole. In general, a factor Xa inhibiting compound of formula I of the instant invention as exemplified herein exhibits a Kass of 0.03 to $2.0 \times 10^6$ L/mole or greater. For example a Kass value of $2.12 \times 10^6$ L/mole was measured for the compound of Example 1.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, Biochem. J., 185, 1–11 (1980; and Smith, et al., Biochemistry, 11, 2958–2967, (1972). Human fibrinogen (98 percent pure/ plasmin free) is from American Diagnostica, Greenwich, Conn. Radiolabeling of fibrinogen I-2 preparations is performed as previously reported. Smith, et al., Biochemistry, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 μg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, Biochem. J., 185, 1–11 (1980); and Smith, et al., Biochemistry., 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., Thrombosis Research, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, Br J Pharmacol, 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed witch saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varion) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{\text{Dose } iv}{\text{Dose } po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/− SEM. One-way analysis of variance is used to detect statistically significant differences and then Dunnett's test Is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC) Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-μL sample of citrated (3.8 percent) blood (1 part citrate:9 parts blood) with a hematology analyzer (Cell-Dyn 900, Sequoia-Turner, Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ± SEM. All studies are conducted in accordance with the guiding principles of the American Physiological Society. Further details regarding the procedures are described in Jackson, et al., *J. Cardiovasc. Pharmacol.*, (1993), 21, 587–599.

The abbreviations, symbols and terms used in the examples have the following meanings.

Boc=t-butyloxycarbonyl
Calc=calculated
Cbz=benzyloxycarbonyl
DCC=dicyclohexylcarbodiimide
DMF=dimethylformamide
DMSO=dimethylsulfoxide
EtOAc=ethyl acetate
$Et_2O$=diethyl ether
EtOH=ethanol
Fmoc=9-fluorenylmethoxy-carbonyl
Fmoc-OSu=9-fluorenylmethyl N-succinimidyl carbonate
HOAC=acetic acid
HOAt=1-hydroxy-7-azabenzotriazole
HOBt=1-hydroxybenzotriazole
HPLC=High Performance Liquid Chromatography
MS=mass spectrum
RP-HPLC=Reversed Phase High Performance Liquid Chromatography
TFA=trifluoroacetic acid
THF=tetrahydrofuran
TLC=thin layer chromatography The following Examples are provided to further describe the invention and are not to be construed as limitations thereof.

The $R_f$ values in the examples are determined by silica gel thin layer chromatography (Kieselgel 60 F-254) in the following systems:

(A) Chloroform-Methanol-Acetic Acid (135:15:1);
(B) Chloroform-Methyl alcohol (9:1);
(C) Chloroform-Ethyl Acetate (8:2);
(D) Chloroform-Ethyl Acetate (1:1).

EXAMPLE 1

Preparation of 3-[(6-Indolyl)carbonyl]amino-1-[[1-(4-pyridinyl)piperidin-4-yl]carbonyl]pyrrolidine Hydrochloride Salt.

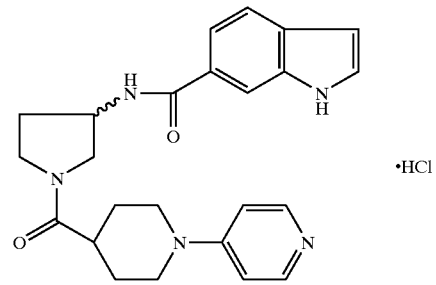

A. 1-Cbz-3-(t-butyloxycarbonyl)aminopyrrolidine

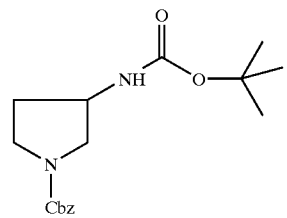

To a solution of 3-(t-butyloxycarbonyl)aminopyrrolidine (5.0 g, 26.8 mmol) in THF (40 mL) was added triethylamine (3.7 mL, 26.8 mmol), followed by the addition of benzyl chloroformate (3.8 mL, 26.8 mmol) slowly. After the reaction mixture was stirred for 24 h at room temperature, the reaction mixture was filtered and solvent removed in vacuo. The residue was dissolved in EtOAc and washed sequentially with 1 N $NaHCO_3$ (100 mL), 1.5 N citric acid (100 mL), and water. The organic layer was dried ($MgSO_4$) and concentrated to dryness in vacuo to give the title compound (7.13 g, 83%).

TLC $R_f$ (C) 0.41;
MS 321 $(M+H)^+$;
Analysis for $C_{17}H_{24}N_2O_4$: Calcd: C, 63.73; H, 7.55; N, 8.74; Found: C, 64.01, H, 7.39, N, 8.71.

B. 1-Cbz-3-[(6-indolyl)carbonyl]aminopyrrolidine

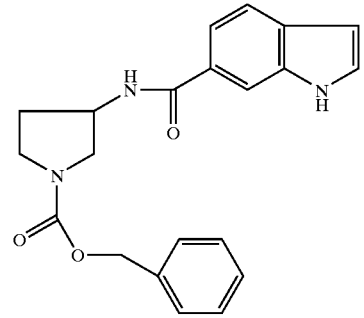

The above compound from Part A (3.15 g, 9.8 mmol) was placed in a flask containing trifluoroacetic acid (30 mL) and anisole (3.0 mL), and stirred at 0° C. for 20 min. The reaction was concentrated in vacuo without heating, and diethyl ether (100 mL) was added. The resulting solid was filtered, washed with diethyl ether, and dried in vacuo to give 3.07 g of the amine TFA salt.

The amine salt (3.07 g) was dissolved in EtOAc (200 mL) and washed sequentially with 1 N $NaHCO_3$ and water. The organic layer was dried (MgSO$_4$) and evaporated in vacuo to an amorphous solid. The solid (0.6 g, 2.72 mmol) was dissolved in DMF (20 mL) and stirred at room temperature. To the solution was added indole-6-carboxylic acid (0.71 g, 2.72 mmol), HOBt (0.37 g, 2.72 mmol), and DCC (0.56 g, 2.72 mmol). The reaction was stirred for 24 hours at room temperature. The resultant precipitate was removed by filtration, and the mother liquor was concentrated in vacuo to an oil. The oil was dissolved in EtOAc (250 mL) and washed sequentially with 1 N NaHCO$_3$, water, 1.5 N citric acid, and water. The organic layer was dried (MgSO$_4$) and evaporated in vacuo to an amorphous solid of the crude title compound (0.53 g, 53%).
TLC R$_f$ (D) 0.21;
MS 364 (M+H)$^+$;
Analysis for C$_{21}$H$_{21}$N$_3$O$_3$: Calcd: C, 69.41; H, 5.82; N, 11.56; Found: C, 69.37, H, 6.08, N, 11.50.

C. 1-Cbz-3-[[1-(t-butyloxycarbonyl)indol-6-yl]carbonyl]aminopyrrolidine

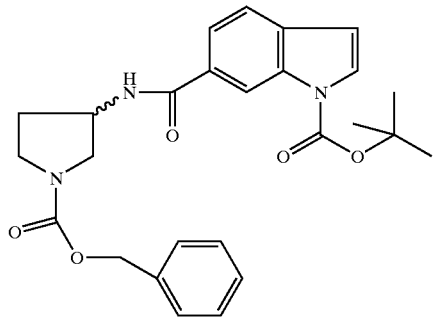

The amorphous crude solid compound from Part B (0.99 g, 2.72 mmol) was dissolved in CH$_3$CN (20 mL) and CH$_2$Cl$_2$ (5 mL). To the solution was added 4-dimethylaminopyridine (0.33 g, 2.72 mmol), diisopropylethylamine (0.47 mL, 2.72 mmol), and di-tert-butyl dicarbonate (0.66 mL, 2.86 mmol). After the reaction mixture was stirred for 24 hours, the reaction mixture was concentrated in vacuo to an oil. The oil was dissolved in EtOAc (250 mL) and washed sequentially with 1 N NaHCO$_3$, water, 1.5 N citric acid, and water. The organic layer was dried (MgSO$_4$) and evaporated in vacuo to an amorphous solid of the crude title compound (1.25 g, 99%).
TLC R$_f$ (D) 0.62;
MS 464 (M+H)$^+$;
Analysis for C$_{26}$H$_{29}$N$_3$O$_5$: Calcd: C, 67.37; H, 6.31; N, 9.07; Found: C, 67.66; H, 6.26; N, 9.22.

D. 3-[(6-Indolyl)carbonyl]amino-1-[[1-(4-pyridinyl)piperidin-4-yl]carbonyl]pyrrolidine Hydrochloride The amorphous crude solid compound from Part C (1.25 g, 2.69 mmol), dissolved in ethanol (100 mL) and 1 N HCl (2.7 mL, 2.69 mmol), was hydrogenated in the presence of 5% Pd/C catalyst (0.30 g) at ambient temperature and pressure. After the reaction was completed, the catalyst was removed by filtration. The filtrate was concentrated in vacuo and dried overnight. The solid was triturated with Et$_2$O, filtered, and dried to give 3-[[1-(t-butyloxycarbonyl)indol-6-yl]carbonylamino]pyrrolidine hydrochloride salt (0.93 g).

In a separate flask [1-(4-pyridinyl)piperidin-4-yl]-carboxylic acid (0.76 g, 3.69 mmol) was suspended in CH$_2$Cl$_2$ (30 mL), and thionyl chloride (0.4 mL, 5.53 mmol) was added. The reaction was refluxed for 2 h, and the solvent was removed in vacuo. The residue was dissolved in CH$_2$Cl$_2$ (25 mL) and added to a solution containing the above hydrochloride salt (0.93 g), diisopropylethylamine (0.43 mL, 2.46 mmol), and pyridine (3 mL). The reaction mixture was stirred for 24 h at room temperature. The resultant solution was concentrated in vacuo and dried overnight to give an oil (2.53 g). The oil (2.53 g) was placed in a flask containing trifluoroacetic acid (20 mL), anisole (2.0 mL) and stirred at 0° C. (30 min). The reaction was concentrated in vacuo without heating, and diethyl ether (100 mL) was added. The resulting solid was filtered, washed with diethyl ether, and dried in vacuo to give 1.65 g of the title compound. The 1.65 g of crude product was purified using a 5×25 cm chromatography column with C$_{18}$ resin, and a gradient of increasing concentrations of 0.01% HCl/CH$_3$CN (5% to 40%) was used to elute the product from the column. Fractions were collected and pooled on the basis of analytical RP-HPLC profile and lyophilized to afford pure title compound as a white solid (0.747 g, 56%).

MS 418 (M+H)$^+$.

EXAMPLE 2

Preparation of 3S-[(6-Indolyl)carbonyl]amino-1-[[1-(4-pyridinyl)piperidin-4-yl]carbonyl]pyrrolidine Dihydrochloride Salt.

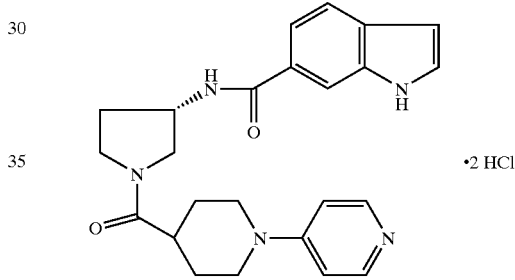

A. 1-t-Butyloxycarbonylindole-6-carboxylic Acid

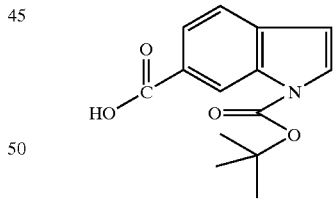

To a suspension of indole-6-carboxylic acid (2.5 g, 15.5 mmol) in CH$_3$CN (5 mL) and DMF (20 mL) was added 4-dimethylaminopyridine (1.9 g, 15.5 mmol), diisopropylethylamine (2.7 mL, 15.5 mmol), and di-tert-butyl dicarbonate (3.7 mL, 16.3 mmol). After the reaction mixture was stirred for 24 h at room temperature, the reaction solvent was removed in vacuo; and the residue was suspended in 1 N NaHCO$_3$ (100 mL) and Et$_2$O (100 mL). The aqueous layer was separated and extracted with Et$_2$O (2×200 mL). The aqueous layer was acidified to pH 2.5 with 5 N HCl and extracted with EtOAc (500 mL). The organic layer was dried (MgSO$_4$) and concentrated to dryness in vacuo to give the title compound (2.35 g, 58%).

TLC $R_f$ (B) 0.49;
MS 262 (M+H)$^+$;
Analysis for $C_{14}H_{15}NO_4$: Calcd: C, 64.36; H, 5.79; N, 5.36; Found: C, 66.69, H, 5.43, N, 6.23.

B. 1-Cbz-3S-(t-butyloxycarbonyl)aminopyrrolidine

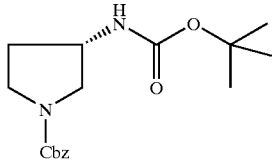

To a solution of 3S-(t-butyloxycarbonyl)aminopyrrolidine (5.0 g, 26.8 mmol) in THF (40 mL) was added triethylamine (3.7 mL, 26.8 mmol), followed by the addition of benzyl chloroformate (3.8 mL, 26.8 mmol) slowly. After the reaction mixture was stirred for 24 h at room temperature, the reaction mixture was filtered and solvent removed in vacuo. The residue was dissolved in EtOAc and washed with 1 N NaHCO$_3$ (100 mL), 1.5 N citric acid (100 mL), and water. The organic layer was dried (MgSO$_4$) and concentrated to dryness in vacuo to give the title compound (7.13 g, 83%).
TLC $R_f$ (C) 0.41;
MS 321 (M+H)$^+$;
Analysis for $C_{17}H_{24}N_2O_4$: Calcd: C, 63.73; H, 7.55; N, 8.74; Found: C, 64.01, H, 7.39, N, 8.71.

C. 1-Cbz-3S-[[1-(t-butyloxycarboxy)indol-6-yl]carbonyl] aminopyrrolidine

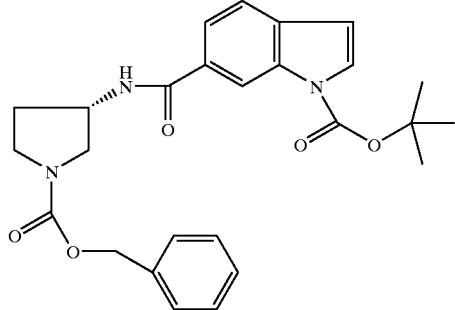

To a solution of the compound from Part B (6.95 g, 21.7 mmol) in glacial HOAc (40 mL) was added anisole (4 mL), and HCl gas was bubbled into reaction for 20 min. The reaction solvent was removed in vacuo and the residue was triturated with Et$_2$O (200 mL). The solid was filtered and dried to give 5.7 g of 1-Cbz-3S-aminopyrrolidine hydrochloride salt.

To a solution of the hydrochloride salt (0.49 g, 1.91 mmol) in DMF (20 mL) was added 1-t-butyloxycarbonylindole-6-carboxylic acid (0.5 g, 1.91 mmol), diisopropylethylamine (0.33 mL, 1.91 mmol), HOBt (0.26 g, 1.91 mmol), and DCC (0.4 g, 1.91 mmol). The reaction was stirred for 24 h at room temperature. The resultant precipitate was removed by filtration, and the mother liquor was concentrated in vacuo to an oil. The resultant oil was dissolved in EtOAc (250 mL) and washed sequentially with 1 N NaHCO$_3$, water, 1.5 N citric acid, and water. The organic layer was dried (MgSO$_4$) and evaporated in vacuo to an amorphous solid of the crude title compound (0.87 g, 98%).
TLC $R_f$ (D) 0.64;
MS 464 (M+H)$^+$.

D. 3S-[(6-Indolyl)carbonyl]amino-1-[[1-(4-pyridinyl) piperidin-4-yl]carbonyl]pyrrolidine Dihydrochloride The amorphous crude solid compound of Part C (0.69 g, 1.49 mmol), dissolved in ethanol (80 mL) and 1 N HCl (1.5 mL, 1.53 mmol), was hydrogenated in the presence of 10% Pd/C catalyst (0.35 g) at ambient temperature and pressure. After the reaction was completed, the catalyst was removed by filtration. The filtrate was concentrated in vacuo and dried overnight. The solid was triturated with Et$_2$O, filtered, and dried to give the hydrochloride salt (0.44 g).

In a separate flask compound [1-(4-pyridinyl)piperidin-4-yl]carboxylic acid (0.18 g, 0.86 mmol) was suspended in CH$_2$Cl$_2$ (25 mL), and thionyl chloride (0.94 mL, 1.29 mmol) was added. The reaction was refluxed for 2 h and the solvent was removed in vacuo. The residue was dissolved in CH$_2$Cl$_2$ (25 mL) and added to a solution containing the hydrochloride salt (0.21 g, 0.57 mmol), diisopropylethylamine (0.1 mL, 0.57 mmol), and pyridine (2 mL). The reaction was stirred for 48 h at room temperature. The resultant solution was concentrated in vacuo and dried overnight to give an oil (0.63 g). The oil (0.63 g) was placed in a flask containing trifluoroacetic acid (10 mL), anisole (1.0 mL) and stirred at 0° C. (30 min). The reaction was concentrated in vacuo without heating and diethyl ether (100 mL) was added. The resulting solid was filtered washed with diethyl ether and dried in vacuo to give 0.34 g of the title compound. The 0.34 g of crude product was purified using a 5×25 cm chromatography column with C$_{18}$ resin, and a gradient of increasing concentrations of 0.01% HCl/CH$_3$CN (5% to 35%) was used to elute the product from the column. Fractions were collected and pooled on the basis of analytical RP-HPLC profile and lyophilized to afford pure title compound as a white solid (0.095 g, 37%).
MS 418 (M+H)$^+$;
Analysis for $C_{24}H_{27}N_5O_2 \cdot 0.2$ HCl: Calcd: C, 58.78; H, 5.96; N, 14.28; Found: C, 60.95, H, 6.31, N, 14.71.

EXAMPLE 3

Preparation of 3R-[(6-Indolyl)carbonyl]]amino-1-[[1-(4-pyridinyl)piperidin-4-yl]carbonyl]pyrrolidine Dihydrochloride Salt.

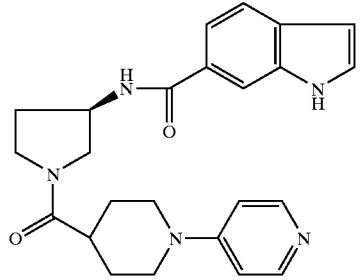

A. 1-t-Butyloxycarbonylindole-6-carboxylic Acid

The title compound was prepared according to the procedure described in Example 2A.

B. 1-Cbz-3R-(t-butyloxycarbonyl)aminopyrrolidine

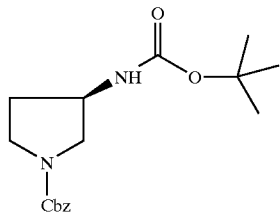

To a solution of 1-Cbz-3R-(t-butyloxycarbonyl) aminopyrrolidine (5.0 g, 26.8 mmol) in THF (40 mL) was added triethylamine (3.7 mL, 26.8 mmol), followed by the addition of benzyl chloroformate (3.8 mL, 26.8 mmol) slowly. After the reaction mixture was stirred for 24 h at room temperature, the reaction mixture was filtered and solvent removed in vacuo. The residue was dissolved in EtOAc and washed with 1 N NaHCO$_3$ (100 mL), 1.5 N citric acid (100 mL), and water. The organic layer was dried (MgSO$_4$) and concentrated to dryness in vacuo to give the title compound (7.39 g, 86%).
TLC R$_f$ (C) 0.41;
MS 321 (M+H)$^+$;
Analysis for C$_{17}$H$_{24}$N$_2$O$_4$: Calcd: C, 63.73; H, 7.55; N, 8.74; Found: C, 63.51, H, 7.43, N, 8.65.

C. 1-Cbz-3R-[[1-(t-butyloxycarbonyl)indol-6-yl]carbonyl]aminopyrrolidine

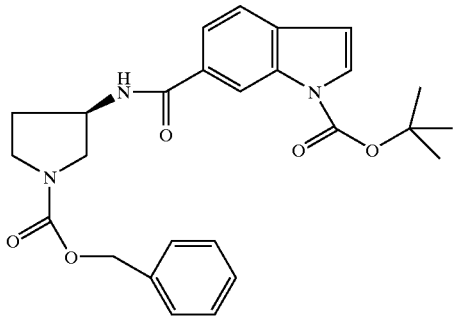

To a solution of the compound of Part B (7.21 g, 22.5 mmol) in glacial HOAc (40 mL) was added anisole (4 mL), and HCl gas was bubbled into reaction for 20 min. The reaction solvent was removed in vacuo, and the residue was triturated with Et$_2$O (200 mL). The solid was filtered and dried to give 5.9 g of 1-Cbz-3R-aminopyrrolidine hydrochloride salt. To a solution of the hydrochloride salt (0.49 g, 1.91 mmol) in DMF (20 mL) was added the compound from Part A (0.5 g, 1.91 mmol), diisopropylethylamine (0.33 mL, 1.91 mmol), HOBt (0.26 g, 1.91 mmol), and DCC (0.4 g, 1.91 mmol). The reaction was stirred for 24 h at room temperature. The resultant precipitate was removed by filtration, and the mother liquor was concentrated in vacuo to an oil. The resultant oil was dissolved in EtOAc (250 mL) and washed sequentially with 1 N NaHCO$_3$, water, 1.5 N citric acid, and water. The organic layer was dried (MgSO$_4$) and evaporated in vacuo to an amorphous solid of the crude title compound (0.88 g, 99%).
TLC R$_f$ (D) 0.64;
MS 464 (M+H)$^+$.

D. 3R-[3-[(6-Indolyl)carbonyl]amino-1-[[1-(4-pyridinyl)piperidin-4-yl]carbonyl]pyrrolidine Dihydrochloride The amorphous crude solid compound from Part C (0.71 g, 1.53 mmol), dissolved in ethanol (80 mL) and 1 N HCl (1.5 mL, 1.53 mmol), was hydrogenated in the presence of 10% Pd/C catalyst (0.28 g) at ambient temperature and pressure. After the reaction was completed, the catalyst was removed by filtration. The filtrate was concentrated in vacuo and dried overnight. The solid triturated with Et$_2$O, filtered, and dried to give 3R-[(1-t-butyloxycarbonyl)indol-6-yl-carbonyl]aminopyrrolidine hydrochloride salt (0.43 g).

In a separate flask compound [1-(4-pyridinyl)piperidin-4-yl]carboxylic acid (0.18 g, 0.86 mmol) was suspended in CH$_2$Cl$_2$ (25 mL), and thionyl chloride (0.94 mL, 1.29 mmol) was added. The reaction was refluxed for 2 h, and the solvent was removed in vacuo. The residue was dissolved in CH$_2$Cl$_2$ (25 mL) and added to a solution containing the above hydrochloride salt (0.21 g, 0.57 mmol), diisopropylethylamine (0.1 mL, 0.57 mmol), and pyridine (2 mL). The reaction was stirred for 24 h at room temperature. The resultant solution was concentrated in vacuo and dried overnight to give an oil (0.58 g). The oil (0.58 g) was placed in a flask containing trifluoroacetic acid (15 mL) and anisole (1.5 mL), and stirred at 0° C. (30 min). The reaction was concentrated in vacuo without heating and diethyl ether (100 mL) was added. The resulting solid was filtered, washed with diethyl ether and dried in vacuo to give 0.31 g of the title compound. The 0.31 g of crude product was purified using a 5×25 cm chromatography column with C$_{18}$ resin, and a gradient of increasing concentrations of 0.01% HCl/CH$_3$CN (5% to 35%) was used to elute the product from the column. Fractions were collected and pooled on the basis of analytical RP-HPLC profile and lyophilized to afford pure title compound as a white solid (0.078 g, 3%).

MS 418 (M+H)$^+$;
Analysis for C$_{24}$H$_{27}$N$_5$O$_2$0.2 HCl: Calcd: C, 59.96; H, 5.96; N, 14.28; Found: C, 59.96, H, 6.29, N, 14.57.

EXAMPLE 4

Preparation of 3-[(5-Benzimidazolyl)carbonyl]amino-1-[[1-(4-pyridinyl)piperidin-4-yl]carbonyl]pyrrolidine Dihydrochloride.

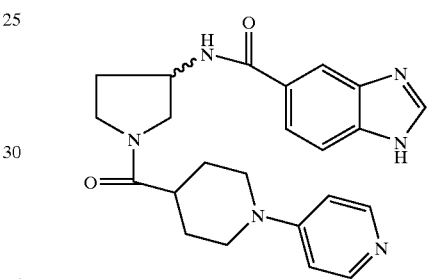

A. 1-t-Butyloxycarbonylbenzimidazole-5-carboxylic Acid

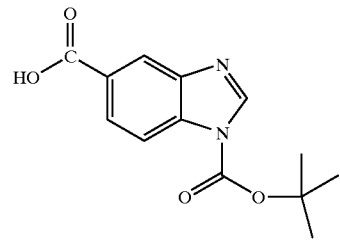

To a suspension of benzimidazole-5-carboxylic acid (5.0 g, 30.8 mmol) in DMF (50 mL) was added 4-dimethylamino-pyridine (3.77 g, 30.8 mmol), diisopropylethylamine (5.37 mL, 30.8 mmol), and di-tert-butyl dicarbonate (7.5 mL, 32.4 mmol). The reaction mixture was initially heated to 60° C. for 30 min and then cooled to room temperature and stirred for 24 h. The reaction solvent was removed in vacuo and the residue was suspended in 1 N NaHCO$_3$ (100 mL) and Et$_2$O (100 mL). The aqueous layer was separated and extracted with Et$_2$O (2×200 mL). The aqueous layer was acidified to pH 2.8 with 5 N HCl and extracted with EtOAc (500 mL). The organic layer was dried (MgSO$_4$) and concentrated to dryness in vacuo to give the title compound (5.6 g, 70%).

TLC R$_f$ (B) 0.52;
MS 263 (M+H)$^+$.

B. 1-Cbz-(t-butyloxycarbonyl)aminopyrrolidine

The title compound may be prepared according to the procedure described in Example 1A.

C. 1-Cbz-3-[[1-(t-butyloxycarbonyl)benzimidazol-5-yl]carbonyl]aminopyrrolidine

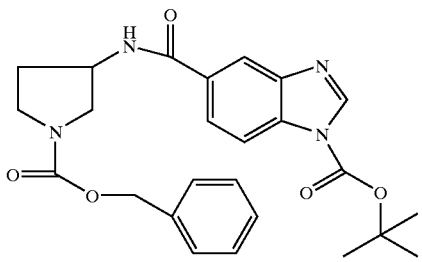

To a solution of the compound from Part B (6.95 g, 21.7 mmol) in glacial HOAC (40 mL) was added anisole (4 mL), and HCl gas was bubbled into reaction for 20 min. The reaction solvent was removed in vacuo, and the residue was triturated with Et$_2$O (200 mL). The solid was filtered and dried to give 5.7 g of 1-Cbz-3-aminopyrrolidine hydrochloride salt.

To a solution of the hydrochloride salt (0.49 g, 1.91 mmol) in DMF (20 mL) was added 1-t-butyloxycarbonylbenzimidazole-5-carboxylic acid (0.5 g, 1.91 mmol), diisopropylethylamine (0.33 mL, 1.91 mmol), HOBt (0.26 g, 1.91 mmol), and DCC (0.4 g, 1.91 mmol). The reaction was stirred for 24 h at room temperature. The resultant precipitate was removed by filtration, and the mother liquor was concentrated in vacuo to an oil. The resultant oil was dissolved in EtOAc (250 mL) and washed sequentially with 1 N NaHCO$_3$, water, 1.5 N citric acid, and water. The organic layer was dried (MgSO$_4$) and evaporated in vacuo to an amorphous solid of the crude title compound (0.78 g, 88%).

TLC R$_f$ (B) 0.64;

D. 3-[(5-Benzimidazolyl)carbonyl]amino-1-[[1-(4-pyridinyl)piperidin-4-yl]carbonyl]pyrrolidine Dihydrochloride The amorphous crude solid of the compound from Part C (0.75 g, 1.61 mmol), dissolved in ethanol (80 mL) and 1 N HCl (1.6 mL, 1.61 mmol), was hydrogenated in the presence of 5% Pd/C catalyst (0.53 g) at ambient temperature and pressure. After the reaction was completed, the catalyst was removed by filtration. The filtrate was concentrated in vacuo and dried overnight. The solid was triturated with Et$_2$O, filtered, and dried to give 3-[[1-(t-butyloxycarbonyl)benzimidazol-5-yl]carbonyl]aminopyrrolidine hydrochloride salt (0.44 g).

In a separate flask CH$_2$Cl$_2$ (25 mL) and thionyl chloride (0.94 mL, 1.29 mmol) was added to 1-(4-pyridinyl)piperidin-4-ylcarboxylic acid (0.18 g, 0.86 mmol) suspended in CH$_2$Cl$_2$ (10 mL). The reaction mixture was refluxed for 2 h and solvent removed in vacuo. The resulting oil was dissolved in CH$_2$Cl$_2$ (20 mL); and the hydrochloride salt (0.21 g, 0.57 mmol) from above was added, followed by diisopropylethylamine (0.1 mL, 0.57 mmol) and pyridine (3 mL). The reaction was stirred for 24 h at room temperature, and the solvent was removed in vacuo to give a brown solid (0.49 g).

The solid (0.49 g) was placed in a flask containing trifluoroacetic acid (15 mL), anisole (1.5 mL) and stirred at 0° C. for 20 min. The reaction was concentrated in vacuo without heating and diethyl ether (100 mL) was added. The resulting solid was filtered, washed with diethyl ether, and dried in vacuo to give 0.49 g of the crude title compound. The 0.49 g of crude product was purified using a 5×25 cm chromatography column with C$_{18}$ resin, and a gradient of increasing concentrations of 0.01% HCl/CH$_3$CN (2% to 25%) was used to elute the product from the column. Fractions were collected and pooled on the basis of analytical RP-HPLC profile and lyophilized to afford pure title compound as a white solid (0.073 g, 9%).

MS 419 (M+H)$^+$;

Analysis for C$_{23}$H$_{26}$N$_6$O$_2$.2 HCl.1.5H$_2$O: Calcd: C, 53.29; H, 6.03; N, 16.21; Found: C, 53.30, H, 6.15, N, 16.00.

EXAMPLE 5

Preparation of 3-[[1-(4-Pyridinyl)piperidin-4-yl]carbonyl]amino-1-[(6-indolyl)carbonyl]pyrrolidine Dihydrochloride.

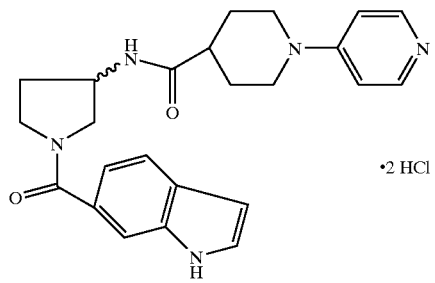

A. 1-t-Butyloxycarbonylindole-6-carboxylic acid

The title compound was prepared according to the procedure described in Example 2A.

B. 1-Cbz-3-(t-butyloxycarbonyl)aminopyrrolidine

The title compound was prepared according to the procedure described in Example 1A.

C. 1-Cbz-3-[(9-fluorenyl)methoxycarbonyl]aminopyrrolidine

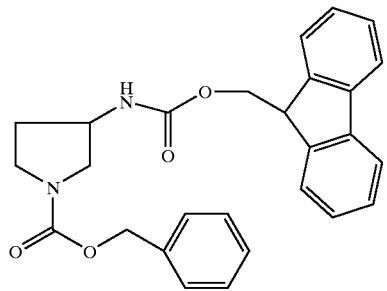

To a solution of the compound from Part B (6.95 g, 21.7 mmol) in glacial HOAc (40 mL) was added anisole (4 mL) and HCl gas was bubbled into reaction for 20 min. The reaction solvent was removed in vacuo, and the residue was triturated with Et$_2$O (200 mL). The solid was filtered and dried to give 5.7 g of 1-Cbz-3-aminopyrrolidine hydrochloride salt. To a solution of the hydrochloride salt (1.5 g, 5.8 mmol) in dioxane (20 mL) water (20 mL) was added Fmoc-OSu (1.97 g, 5.84 mmol) and sodium carbonate (0.61 g, 5.84 mmol). The reaction mixture was stirred for 24 h at room temperature. The reaction mixture was concentrated in vacuo and diluted with EtOAc (200 mL). The resultant solution was washed sequentially with 1 N NaHCO$_3$, water, 1.5 N citric acid, and water. The organic layer was dried (MgSO$_4$) and evaporated in vacuo to an amorphous solid of the crude title compound (2.6 g, 99%).

TLC R$_f$ (C) 0.44;

MS 443 (M+H)$^+$;

Analysis for C$_{27}$H$_{26}$N$_2$O$_4$: Calcd: C, 73.29; H, 5.92; N, 6.33; Found: C, 73.27, H, 6.01, N, 6.50.

D. 3-[(Fluorenyl)methyoxycarbonyl]amino-[[1-(t-butyloxycarbonyl)indol-6-yl]carbonyl]pyrrolidine

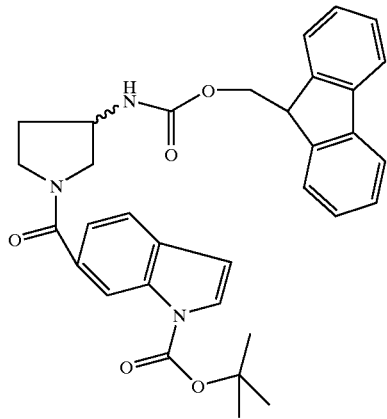

The solid compound from Part C (2.58 g, 5.8 mmol), dissolved in ethanol (125 mL) and 1 N HCl (5.8 mL, 5.8 mmol), was hydrogenated in the presence of 5% Pd/C catalyst (0.7 g) at ambient temperature and pressure. After the reaction was completed, the catalyst was removed by filtration. The filtrate was concentrated in vacuo and dried overnight. The solid triturated with Et$_2$O, filtered, and dried to give 3-[(fluorenyl)methyoxycarbonyl]aminopyrrolidine hydrochloride salt (1.65 g).

To a solution of the hydrochloride salt (0.66 g, 1.91 mmol) in DMF (20 mL) was added the compound from Part A (0.5 g, 1.91 mmol), diisopropylethylamine (0.33 mL, 1.91 mmol), HOBt (0.26 g, 1.91 mmol), and DCC (0.4 g, 1.91 mmol) The reaction was stirred for 24 h at room temperature. The resultant precipitate was removed by filtration, and the mother liquor was concentrated in vacuo to an oil. The resultant oil was dissolved in EtOAc (250 mL) and washed sequentially with 1 N NaHCO$_3$, water, 1.5 N citric acid, and water. The organic layer was dried (MgSO$_4$) and evaporated in vacuo to an amorphous solid of the crude title compound (0.73 g, 69%).

TLC R$_f$ (D) 0.40.

E. 3-[[1-(4-Pyridinyl)piperidin-4-yl]carbonyl]amino-1-[(6-indolyl)carbonyl]pyrrolidine Dihydrochloride The amorphous crude solid compound from Part D (0.7 g, 1.27 mmol) was dissolved in 20% piperidine in DMF (20 mL) and stirred at room temperature for 25 min. After the reaction was completed the solution was concentrated in vacuo. The solid was triturated with hexane, filtered, and dried to give free 1-[1-(t-butyloxycarbonyl)indol-6-yl)carbonyl]-3-aminopyrrolidine (0.39 g).

In a separate flask compound [1-(4-pyridinyl)piperidin-4-yl]carboxylic acid (0.21 g, 1.0 mmol) was suspended in CH$_2$Cl$_2$ (25 mL), and thionyl chloride (0.11 mL, 1.5 mmol) was added. The reaction mixture was refluxed (2 h) and the solvent was removed in vacuo. The residue was dissolved in CH$_2$Cl$_2$ (25 mL) and added to a solution containing the free base (0.22 g, 0.67 mmol) in CH$_2$Cl$_2$ (15 mL) and pyridine (3 mL). The reaction mixture was stirred for 48 h at room temperature. The reaction mixture was concentrated in vacuo and dried overnight to give an oil (0.49 g).

The oil (0.49 g) was placed in a flask containing trifluoroacetic acid (20 mL), anisole (2.0 mL) and stirred at 0° C. for 25 min. The reaction was concentrated in vacuo without heating and diethyl ether (100 mL) was added. The resulting solid was filtered, washed with diethyl ether, and dried in vacuo to give 0.49 g of the title compound. The 0.49 g of crude product was purified using a 5×25 cm chromatography column with C$_{18}$ resin, and a gradient of increasing concentrations of 0.01% HCl/CH$_3$CN (5% to 40%) was used to elute the product from the column. Fractions were collected and pooled on the basis of analytical RP-HPLC profile and lyophilized to afford pure title compound as a white solid (0.050 g, 2%).

MS 418 (M+H)$^+$;

Analysis for C$_{24}$H$_{27}$N$_5$O$_2$.2HCl.0.5 H$_2$O: Calcd: C, 57.72; H, 6.05; N, 14.02; Found: C, 57.14, H, 5.76, N, 13.76.

EXAMPLE 6

Preparation of 3S-[(6-Indolyl)carbonyl)]amino-1-[[1-(4-pyridinyl)piperidin-4-yl]methoxycarbonyl]pyrrolidine

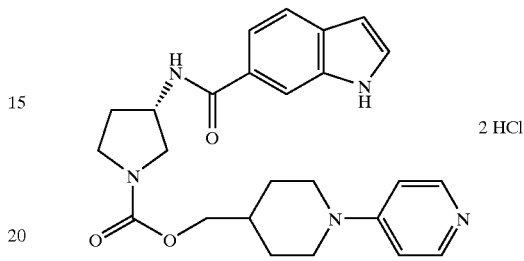

A. 1-t-Butyloxycarbonylindole-6-carboxylic Acid

The title compound was prepared by the procedures described in Example 2A.

B. 1-Cbz-3S-(t-Butyloxycarbonyl)aminopyrrolidine

The title compound was prepared according to the procedure described in Example 2B.

C. 1-Cbz-3S-[[1-(t-Butyloxycarbonyl)indol-6-yl]carbonyl]aminopyrrolidine

The title compound was prepared according to the procedure described in Example 2C.

D. 3S-[(6-Indolyl)carbonyl)]amino-1-[[1-(4-pyridinyl)piperidin-4-yl]methoxycarbonyl]pyrrolidine The amorphous crude solid compound from part Part C (0.69 g, 1.5 mmol), dissolved in ethanol (80 mL) and 1 N HCl (1.5 mL, 1.5 mmol) was hydrogenated in the presence of 10% Pd/C catalyst (0.3 g) at ambient temperature and pressure. After the reaction was completed, the catalyst was removed by filtration. The filtrate was concentrated in vacuo and dried overnight. The solid was triturated with Et$_2$O, filtered, and dried to give 3S-[[1-(t-butyloxycarbonyl)-indol-6-yl]carbonyl]aminopyrrolidine hydrochloride salt (0.44 g).

In a separate flask to CH$_2$Cl$_2$ (20 mL) was added phosgene (20% in toluene, 0.28 mL, 0.55 mmol), and the solution stirred at room temperature. 1-(4-Pyridinyl)piperidine-4-methanol (0.11 g, 0.55 mmol) suspended in CH$_2$Cl$_2$ (10 mL) was added to the reaction mixture. The reaction mixture was stirred at room temperature for 5 min; then the hydrochloride salt (0.2 g, 0.55 mmol) from above was added, followed by triethylamine (0.08 mL, 0.55 mmol). The reaction mixture was stirred for 1.5 h, and the solvent was removed in vacuo to give a brown solid (0.47 g).

The solid (0.47 g) was placed in a flask containing trifluoroacetic acid (15 mL) and anisole (1.5 mL), and stirred at 0° C. for 25 min. The reaction mixture was concentrated in vacuo without heating, and diethyl ether (100 mL) was added. The resulting solid was filtered, washed with diethyl ether, and dried in vacuo to give 0.38 g of the title compound. The 0.38 g of crude product was purified using a 5×25 cm chromatography column with C$_{18}$ resin, and a gradient of increasing concentrations of 0.01% HCl/CH$_3$CN (2% to 30%) was used to elute the product from the column. Fractions were collected and pooled on the basis of analytical RP-HPLC profile and lyophilized to afford pure title compound as a white solid (0.044 g, 2%).

MS 448 (M+H)$^+$;

Analysis for C$_{25}$H$_{29}$N$_5$O$_3$.2 HCl: Calcd: C, 57.69; H, 6.00; N, 13.46; Found: C, 57.50, H, 6.05, N, 13.16.

EXAMPLE 7

Preparation of (2S,4S)-4-[[1-(4-Pyridinyl)piperidin-4-yl]carbonyl]amino-1-[(6-indolyl)carbonyl]pyrrolidine-2-carboxylic Acid.

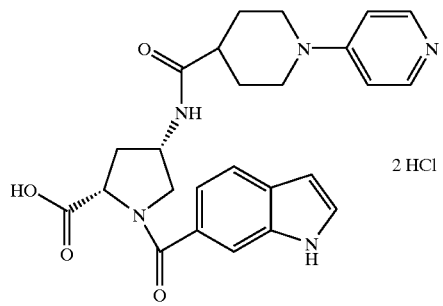

A. 1-t-Butyloxycarbonylindole-6-carboxylic acid

The title compound was prepared according to the procedure described in Example 2A.

B. (2S,4S)-4-[[(9-Fluorenyl)methoxy]carbonyl]amino-1-[[1-(t-butyloxycarbonyl)indol-6-yl]carbonyl]pyrrolidine-2-carboxylic Acid

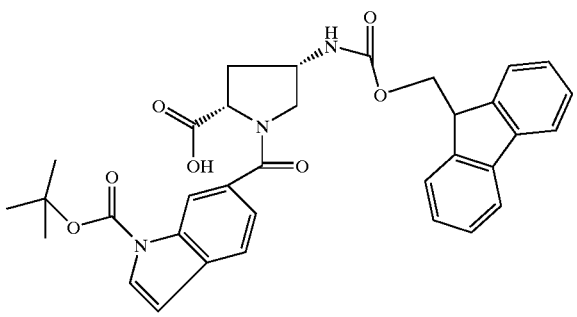

(2S,4S)-4-(Fmoc-amino)-1-Boc-pyrrolidine-2-carboxylic acid (0.5 g, 1.1 mmol) was placed in a flask containing trifluoroacetic acid (20 mL) and anisole (2.0 mL), and stirred at 0° C. for 20 min. The reaction was concentrated in vacuo without heating, and diethyl ether (100 mL) was added. The resulting solid was filtered, washed with diethyl ether, and dried in vacuo to give (0.5 g, 97%) of the crude TFA salt of (2S,4S)-4-(Fmoc-amino)pyrrolidine-2-carboxylic acid.

In a separate flask the compound from Example 7, Part A (0.14 g, 0.54 mmol) was suspended in CH$_2$Cl$_2$ (10 mL), and pyridine (0.044 mL, 0.54 mmol) was added. To the reaction mixture oxalyl chloride (0.47 mL, 0.54 mmol) was added, and the reaction mixture was stirred at room temperature for 5 min. The reaction solvent was removed in vacuo. The resulting oil was dissolved in CH$_2$Cl$_2$ (10 mL) and DMSO (10 mL) and added to a solution of the above TFA salt (0.25 g, 0.55 mmol), CH$_2$Cl$_2$ (5 mL), and pyridine (0.13 mL, 1.6 mmol). After the reaction mixture was stirred for 4 h, the reaction solvent was removed in vacuo. The resultant oil was dissolved in EtOAc (250 mL) and washed sequentially with 1.5 N citric acid, and water. The organic layer was dried (MgSO$_4$) and evaporated in vacuo to an amorphous solid of the crude title compound (0.13 g, 39%).

C. (2S,4S)-4-[[1-(4-Pyridinyl)piperidin-4-yl]carbonyl]amino-1-[(6-indolyl)carbonyl]pyrrolidine-2-carboxylic Acid The amorphous crude solid of the compound of Part B (0.13 g, 0.22 mmol) was dissolved in 20% piperidine in DMF (10 mL) and stirred at room temperature for 25 min. The reaction mixture was concentrated in vacuo, and diethyl ether (100 mL) was added. The resulting solid was filtered, washed with diethyl ether, and dried in vacuo to give 0.08 g of crude (2S,4S)-4-amino-1-[1-(t-butyloxycarbonyl)indol-6-yl]carbonylpyrrolidine-2-carboxylic acid.

In a separate flask compound [1-(4-pyridinyl)piperidin-4-yl]carboxylic acid (0.07 g, 0.32 mmol) was suspended in CH$_2$Cl$_2$ (25 mL), and thionyl chloride (0.04 mL, 0.48 mmol) was added. The reaction mixture was refluxed for 2 h and the solvent was removed in vacuo. The residue was dissolved in CH$_2$Cl$_2$ (25 mL) and added to a solution containing the above amine (0.08 g, 0.21 mmol) and pyridine (3 mL). The reaction mixture was stirred for 24 h at room temperature. The resultant solution was concentrated in vacuo and dried overnight to give an oil (0.08 g). The oil (0.08 g) was placed in a flask containing trifluoroacetic acid (15 mL), anisole (1.5 mL) and stirred at 0° C. for 30 min. The reaction mixture was concentrated in vacuo without heating and diethyl ether (100 mL) was added. The resulting solid was filtered, washed with diethyl ether, and dried in vacuo to give 0.2 g of the title compound. The 0.2 g of crude product was purified using a 5×25 cm chromatography column with C$_{18}$ resin, and a gradient of increasing concentrations of 0.01% HCl/CH$_3$CN (2% to 40%) was used to elute the product from the column. Fractions were collected and pooled on the basis of analytical RP-HPLC profile and lyophilized to afford the title compound as a pure white solid (0.006 g, 6%).

What is claimed is:

1. A compound of formula I (or a pharmaceutically acceptable salt thereof)

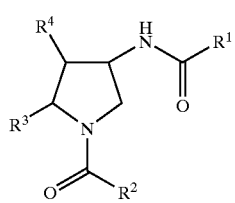

wherein
one of R$^1$ and R$^2$ is Q$^1$; the other of R$^1$ and R$^2$ is Q$^2$;
wherein
Q$^1$ is

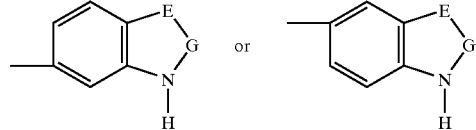

wherein
—E—G—NH— is —C(R$^a$)=CH—NH— in which R$^a$ is hydrogen, fluoro, chloro, bromo or methyl;
Q$^2$ is

in which R$^m$ is 4-pyridyl;
when R$^2$ is Q$^1$, then R$^3$ is H, COOH, N-(methyl)benzenesulfonylamino or phenyl (which may be substituted at the 3- or 4-position with methyl, chloro or fluoro) and R$^4$ is H; and
when R$^2$ is Q$^2$, then R$^3$ is H and R$^4$ is H, COOH, methyl, N-(methyl)benzenesulfonylamino, unsubstituted phenyl or phenyl (which may be substituted at the 3- or 4-position with methyl, chloro or fluoro);

or a pharmaceutically acceptable salt of the compound of formula I or prodrug thereof.

2. The compound of claim 1 wherein one of $R^1$ and $R^2$ is $Q^1$ and the other of $R^1$ and $R^2$ is $Q^2$;

$Q^1$ is

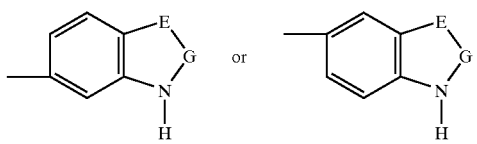

wherein

—E—G—NH— is —CH$_2$=CH$_2$—NH—;

$Q^2$ is

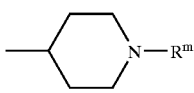

in which $R^m$ is 4-pyridyl;
when $R^2$ is $Q^1$, $R^3$ is H or COOH and $R^4$ is H; and
when $R^2$ is $Q^2$, $R^3$ is H and $R^4$ is H.

3. The compound of claim 1 wherein
$R^1$ is $Q^2$;
$R^2$ is $Q^1$;
$Q^1$ is 6-indolyl;
$Q^2$ is 1-(4-pyridinyl)piperin-4-yl;
$R^3$ is H; and
$R^4$ is H.

4. The compound of claim 1 wherein
$R^1$ is $Q^1$;
$R^2$ is $Q^2$;
$Q^1$ is 6-indolyl;
$Q^2$ is 1-(4-pyridinyl)piperin-4-yl;
$R^3$ is H; and
$R^4$ is H.

5. The pharmaceutically acceptable salt of a compound of formula I as claimed in any of claims 1, 2, 3 and 4 which is an acid-addition salt made from a basic compound of formula I and an acid which provides a pharmaceutically acceptable anion or salt which is made from an acidic compound of formula I and a base which provides a pharmaceutically acceptable cation.

6. A pharmaceutical composition comprising a factor Xa inhibiting compound of formula I, or a pharmaceutically acceptable salt thereof, as claimed in claim 1 in association with a pharmaceutically acceptable carrier, excipient or dilutent.

7. A process for preparing a novel compound of formula I (or a pharmaceutically acceptable salt thereof)

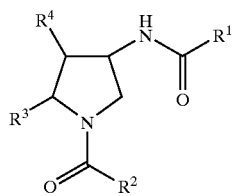

as provided in claim 1 which is selected from
(A) for a compound of formula I in which $R^1$ is $Q^1$, acylating the amino group of a corresponding compound of formula II

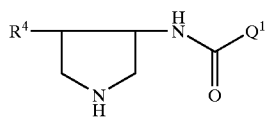

using a corresponding acid of formula $Q^2$-COOH (III) or an activated derivative thereof;
(B) for a compound of formula I in which $R^2$ is $Q^1$, acylating the amino group of a corresponding compound of formula IV

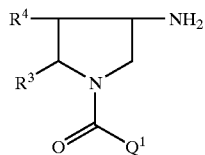

using a corresponding acid of formula $Q^2$-COOH (III) or an activated derivative thereof;
whereafter, for any of the above procedures, when a functional group is protected using a protecting group, removing the protecting group;
whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure;
and wherein, unless otherwise specified, $Q^1$, $Q^2$, $R^1$, $R^2$, $R^3$ and $R^4$ have any of the values defined in claim 1.

8. A method for inhibiting thrombus formation in venous thrombosis, pulmonary embolism or arterial thrombosis comprising administering to a mammal in need of treatment an effective dose of a compound of formula I (or a pharmaceutically acceptable salt thereof) as claimed in claim 1.

* * * * *